United States Patent [19]

Berg et al.

[11] 4,320,201

[45] Mar. 16, 1982

[54] METHOD FOR MAKING COLLAGEN SPONGE FOR MEDICAL AND COSMETIC USES

[75] Inventors: Alexander Berg, Hirschberg; Zdenek Eckmayer, Weinheim, both of Fed. Rep. of Germany

[73] Assignee: Firma Carl Freudenberg, Weinheim, Fed. Rep. of Germany

[21] Appl. No.: 183,485

[22] Filed: Sep. 2, 1980

[51] Int. Cl.³ .............................................. C14C 1/00
[52] U.S. Cl. .................................. 435/265; 435/273; 128/296
[58] Field of Search ................................ 435/273, 265

[56] References Cited

U.S. PATENT DOCUMENTS

| | | | |
|---|---|---|---|
| 2,610,625 | 9/1952 | Sifferd et al. | 128/296 |
| 3,157,524 | 11/1964 | Artandi | 128/296 X |
| 4,220,724 | 9/1980 | Berg et al. | 435/273 |

*Primary Examiner*—Robert J. Warden
*Attorney, Agent, or Firm*—Sprung, Felfe, Horn, Lynch & Kramer

[57] ABSTRACT

A process for producing collagen sponge which is insoluble but highly swellable in water, the sponge having a velour-like surface and being particularly suited for medical and cosmetic applications.

10 Claims, No Drawings

METHOD FOR MAKING COLLAGEN SPONGE FOR MEDICAL AND COSMETIC USES

The present invention relates to a method for making collagen sponge with a velour-like surface which is insoluble, but highly swellable, in water, particularly for use for medical or cosmetic purposes, wherein the collagen-containing tissue serving as raw material, after being dehaired and freed of scar tissue layers, is digested by an alkali and/or acid denaturing process and possibly an enzymatic treatment and then treated with a tanning agent at temperatures below 0° C. and freed of water by freeze drying.

It is known that collagen fibrous materials called collagen sponge are used in medicine and in cosmetics. Such collagen sponges are described for example in German OS No. 2625289 as wound coverings and as filler materials for pathological bone cavities. In making such sponge, the cleaned and desalted collagen-containing raw material is subjected to freeze drying and then sterilized by radiation with gamma rays. Collagen sponges are also described in U.S. Pat. No. 2,610,625. Here too, an acid swollen collagen material is frozen and sublimed under high vacuum.

The collagen sponges obtained by freeze drying according to the afore-named patents are physiologically tolerable and thus can be used effectively for medical applications. The same are, however, soluble in water to a greater or lesser degree so that they lose form and firmness in the presence of water. Furthermore, the acid swelled sponges partially retain the acid used for swelling and thus assume a gel-like appearance as soon as they come in contact with water.

To avoid the presence of acid residues, U.S. Pat. No. 3,157,524 describes a process wherein the residual water and acid are removed by means of solvents. The collagen dispersion is frozen and carefully washed with organic solvents that are miscible with water. As solvent, ammoniacal isopropyl alcohol is suggested among others. This method is expensive, notwithstanding the fact that the cost of freeze drying is eliminated since relatively large amounts of solvents are required which must then be recovered in a time consuming and expensive process. The sponges are physiologically tolerable, but have the serious drawback of not being sufficiently resistant to water.

Water resistant sponges are produced according to German OS No. 1,811,290. A homogeneous collagen paste is mixed with tanning and possibly other agents, frozen, thawed, and the water mechanically removed by squeezing and drying in air. Such sponges can be used also in contact with water. It is preferable in this process to remove the water only by mechanical means. Despite the fact that these per se give good properties, it was found that the added tanning agent is not completely bound or removed, notwithstanding the most scrupulous adherence to the conditions recited so that residues of this tanning agent or reaction products thereof will exercise an irritating effect in subsequent medical or cosmetic applications. In addition, sponges so obtained are brittle and have a rough surface. They become supple again only after moistening but resume this hard and brittle structure upon drying. Thus, although these sponges are resistant to water in contrast to the previously known collagen sponges, they afford only a limited range of application because of the presence of residues and the disagreeably hard structure when dry.

It is thus the object of the present invention to provide a collagen sponge which is resistant to water, that is, practically insoluble in water, but is soft and supple when dry and highly swellable in the presence of water. The collagen sponge is, in addition, physiologically tolerable and produces no irritating effects so that it can be used without any limitations for medical or cosmetic uses.

The above object is achieved according to the invention by a method for making collagen sponge with a velour-like surface that is insoluble, but highly swellable, in water, particularly for use for medical or cosmetic purposes, wherein the collagen-containing tissue serving as raw material, after being dehaired and freed of scar tissue layers, is digested by an alkaline and/or acid denaturing process and possibly an enzymatic treatment and then treated with a tanning agent at temperatures below 0° C. and freed of water by freeze drying. This method is characterized in that the cleaned collagen-containing tissue is subjected to an enzymatic degradation first during an extended period of time, preferably lasting several weeks, with an optionally peroxide-containing, strongly alkaline solution and then for a shorter period of time of one or several days in acid or alkaline medium until the amido nitrogen content of the digested collagen is less than 0.25 mol %, and in that the so obtained suspension of collagen fibers is swollen in acid medium to a vitreous voluminous mass of which a part is then comminuted mechanically to a fiber length of about 1 centimeter and a part, by mincing for example, to a fiber length of about 1 mm so as to form a paste, and the pasty mixture on a dry weight basis comprising about 20 to 60% of the approximately 1 cm long collagen fibers and 80 to 40% of the approximately 1 mm long fibers is diluted with water to an approximately 0.5 to 3.0 wt. % dispersion which is adjusted to a pH value of about 2 to 3.5 and cross-linked and consolidated to a fine-pore sponge of high purity collagen fibers at temperatures below about 0° C. and in the presence of a physiologically tolerable tanning agent and possibly emulsifiers, active substances and the like, and the water is removed from the sturdy sponge by freeze drying.

The cross-linking and consolidation of the collagen sponge is preferably effected in the presence of the tanning agent at a temperature between about $-5°$ and $-60°$ C., and preferably between about $-5°$ and $-40°$ C. As tanning agent (cross-linking agents), aliphatic, aromatic or hydroaromatic diisocyanates are used. The pH during cross-linking is about 3 to 4 and rises during freezing and freeze drying to above about 5. It is preferable to effect the cross-linking in the presence of nonionic emulsifiers and to employ the isocyanate in stoichiometric amount. Particularly suitable are aliphatic diisocyanates, e.g. hexamethylene diisocyanate.

The alkaline degradation of the collagen-containing raw material prior to the enzymatic treatment should take place at a pH above 10, and preferably with a solution, e.g. NaOH in water, which contains about 0.1 to 1.0% $H_2O_2$. The subsequent degradation in the presence of the alkaline or acidic proteinases takes place at pH values of about 9 to 13 and 2 to 5, respectively. Optimum results are obtained if about 0.1 to 1% of urea is added, based on the dry weight of the collagen mass.

Together with the cross-linking agent, emulsifiers such as ethoxylated alkylphenols or alcohols in a concentration of preferably 0.1 to 6 weight % can be added to the collagen paste to be consolidated. As a rule, 1 to 4% of additions, based on the dry weight of the collagen raw material, are used. Softness and fine porosity of the material can thus additionally be influenced. In applications for medical or cosmetic and/or diagnostic purposes, pharmaceutically active ingredients, such as antibiotics, can be added at this stage of the process, concentrations of about 1 to 50% based on the dry weight of the collagen material being particularly preferred.

A particularly supple sponge is obtained when the aqueous collagen-containing mass together with all the additions is shock frozen at a pH between about 2.5 and 3.5 at a temperature between about −20° and −40° C. The shock frozen mass is then subjected to freeze drying in accordance with any of the known methods.

It was found in the implementation of the method according to the invention that a fine, velour-like surface is achieved by the proposed use of two kinds of collagen fibers. According to the invention, therefore, after a maturing process swollen collagen fibers of an average fiber length of about 1 cm are mixed with the pasty suspension of collagen fibers. The long collagen fibers are apparently responsible for the firmness, while the pasty suspension forms the basic material for the pore structure.

It is necessary that both forms of collagen fiber are ripened to such an extent that only a specific amount of the original amido nitrogen remains. In the ripening process, nearly all the accompanying proteins, glycoseaminoglycones, proteoglycones and the like are dissolved and the collagen purified to that extent. About ⅔ of the amide bonds of glutamine and asparagine are removed and a part of the peptide bonds split by cross-linkages.

The alkaline treatment is employed for relatively long periods of time, about 20 to 30 days on the average. The subsequent acid treatment, on the other hand, is of relatively short duration. At that time, strong swelling and an optically visible plasticizing of the materials occurs.

The maturing process of the collagen material is checked analytically. To that end, the amido nitrogen content and the related shift of the isoelectric point toward the acid side should be monitored. The amido nitrogen content of fresh, untreated collagen is usually about 0.7 mol %. In the mass pretreated for sponge production according to the invention the amido nitrogen content is necessarily only 0.25 mol % maximum.

As a rule, the following procedure is employed;

a. The raw material, after dehairing and removal of scar tissue layers, is first treated with 0.3–1.5 wt.%—aqueous caustic soda containing 0.1 to 1.0% hydrogen peroxide for a period of 1 to 5 days. Following that, the mixture is subjected to the action of 0.1 to 1.0%—aqueous solution of sodium hydroxide or calcium hydroxide until the amido nitrogen content has reached a value of above 0.24 mol %. The hydrogen peroxide serves to brighten and plasticize the material and shortens the digestion process. In place of hydrogen peroxide, salts such as sodium peroxide or peroxides of organic acids may be used.

The enzymatic treatment takes place at temperatures up to 35° C., and preferably about 30° C. The degradation can be effected for example with pronase (proteolytic enzyme of Streptomyces griseus) in acid medium at a pH of 2.0 to 3.0 or with alkaline proteinases of bacterial origin in alkaline medium at pH 9 to 13. Other proteinases which can be employed include those from *Bacillus alkanophillis, Bacillus firmus, Bacillus licheniformis, Aspergillus Oryzae* and *Aspergillus Saitoi.* According to the invention, an addition of between 0.1 and 1.0 mol % urea during the enzymatic treatment is suggested. This results in a shorter treatment period and in a better product.

The proteolytic effectiveness of the enzymes is conveniently determined according to the "Löhlein-Volhard method" and is expressed in "LVU" (Löhlein-Volhard units). One LVU represents that amount of enzyme which under the specific conditions of the method digests, 1.725 mg of casein. According to the invention, enzymes of about 9000 LVU are used in amounts of about 0.1 to 5 wt. %.

The enzymatic treatment speeds up the maturing process and shortens the treatment to about one week. The proteolytic enzymes first attack the non-collagen protein substances, while the collagen remains preserved in its pure form.

b. The collagen material treated in alkaline medium and possibly also treated with peroxides and enzymes is now subjected to an acid treatment prior to separation into long and short fibers. This stage of the process results in a volume increase which can be controlled by the determination of the solid content. Preferably the treatment is continued up to a dry weight of 12 to 14 wt. % (remainder water). Vitrification of the raw material can be observed visually.

The acid treatment is preferably effected with hydrochloric acid or acetic acid. However, the kind of acid to be chosen will be determined by the required degree of purity of the material and the desired swelling action. Generally, 3% hydrochloric acid in 4 hours will give a dry weight of 10 to 15 wt. %, which is useful for most purposes. The material is then washed with running water until the pH value is about 3.0.

In the acid treatment, even the last residues of acid-soluble protein products or decomposition products are removed from the material and at the same time any remaining alkali is neutralized and washed out. The main fiber structure is additionally loosened up so as to facilitate the subsequent mechanical treatment (separation into fibers).

c. The collagen material, treated with alkali and acid and digested, is now mechanically prepared for the sponge material according to the invention. To that effect, two kinds of fiber are produced which are then mixed together in recited ratio.

1. Collagen fibers with an average fiber length of about 1 cm are produced by mechanical disintegration of the collagen lumps, e.g. by squeezing and subsequent shrinking of the fiber mass by addition of salts or salt solutions (common salt for example). The concentration of the common salt should be about 10%.

2. The collagen paste serving as starting product for the 1 mm fibers can be produced by repeated grinding of the same (alkaline-and acid-treated) material in a meat grinder and subsequent repeated homogenization and comminution of the mass in a colloid mill.

The two kinds of collagen fibers are mixed in a ratio of 20 to 60% long fibers and 80 to 40% short fibers. The long collagen fibers are washed with running water prior to mixing, the pH value adjusted with acid to 2.0 to 3.5, and the fibers stirred until they have uniformly swelled. They are then mixed into the finefiber paste.

d. The tanning and/or cross-linking of the collagen paste under formation of the sponge material according to the invention is carried out with physiologically compatible tanning substances, such as hexamethylene-diisocyanate. Where allergic or irritating effects are not expected one may also use aldehydes, such as glutaric aldehyde or formaldehyde. However, diisocyanates are generally preferred because of their high compatibility. In the tanning and/or cross-linking, the isocyanate groups react with the amino groups of the collagen with formation of urea derivatives which are completely harmless physiologically. The bifunctional isocyanates combine with two different protein chains and thus create a spatial linkage. By changing the kind and amount of diisocyanate it becomes possible to vary the molecular weight, the degree of cross-linkage and thus also the physical properties of the end product. Additional use of non-ionic emulsifiers is preferred.

After addition of the cross-linking agent, the material is quickly cooled to a temperature below 0° C. (shock frozen). Preferably, the range between −5° and −40° C. is chosen. The material is then freeze dried to remove the water. Prior to addition of the tanning agent, i.e. cross-linking agent, the pH of the mass is 3.0 to 4.0. The pH slowly increases during the freezing process to a value of 4.0 to 6.0.

Preferably, the tanning or cross-linking agent is added only up to the stoichiometrically calculated amount, i.e. in smaller amounts. The cross-linking reaction itself proceeds at a very slow rate, the dewatering by freeze drying additionally constituting highly favorable conditions for the cross linking reaction. Generally, a concentration of about 2 mol % of cross-linking agent is used.

e. The sponge according to the invention is distinguished from other known collagen sponges by the fact that it is physiologically compatible and thus can be used without restriction for all medical and cosmetic applications. It is insoluble, but highly swellable in water. In contrast to the collagen sponge according to German OS No. 1,811,290 which is likewise insoluble and swellable in water it is, however very supple when dry, and has a velour-like hand. It is obvious that such a universally usable collagen sponge should be mixed with all kinds of admixtures. This too is possible practically without limitation. Active ingredients of whatever kind are worked into the end product preferably during the cross-linking process. The elastic properties of the collagen sponge can be used for cosmetic applications. Besides purely pharmaceutically active additions, there may be used for cosmetic purposes known per se additions for treating dry, fatty or ageing skin, and likewise disinfectants, antibiotics and the like.

The following examples will explain more fully the method according to the invention:

EXAMPLE 1

Hides from necks of freshly slaughtered cattle are prepared by soaking, seeping and separating of the scar tissue layers according to the methods generally used in leather production and then washed with fresh water in a hollander for a period of ½ hour. The material is then treated for one day with a 1%-sodium hydroxide solution and 0.3%-hydrogen peroxide solution. This is followed by washing in the hollander with running water. The amido nitrogen content is now 0.45%.

In further course of the process, the material is treated with a mixture of sodium hydroxide and calcium hydroxide. The ratio of hide to washing solution is 1:2; the sodium hydroxide proportion is 0.5 wt. %, relative to the weight of the hide. The material is thoroughly stirred once each day. Duration of treatment is about 25 days. Amido nitrogen: 0.20%.

The alkali treatment is followed by the acid treatment. To that end, the material is acidified in a tanning vat with hydrochloric acid. Then, 10 wt. % of hydrochloric acid based on hide weight, are added. The ratio of hide to washing solution is about 1 to 1, and the duration of treatment is 6 hours. The pH at the end of the treatment is 0.8 to 1.2. Thereafter, the material is washed with running water in the vat until the pH of the raw material is 3.0. After the treatment, the collagen material has a dry weight of 14 wt. %.

The material so treated is now divided into two parts: the first part is used for making fibers, and the second part serves for producing the short-fiber mass.

a. Fibers:

The material is cut into pieces of about 30×10 cm and broken up with fluted rollers. The treatment is repeated 4 to 6 times, the pressure being increased with each new calendering. 10 wt. % of solid common salt and 50 wt. % of water, relative to the weight of hide, are now added to the mass of swollen fibers. The mass is then left standing for about 2 hours, washed briefly with running water and then centrifuged. After centrifuging, the dry weight is about 30 wt. %. The material is diluted with water to a dry weight of 2.2% and the pH adjusted to 3.0. The material is stirred until all fibers have swelled uniformly and the mass is homogeneous.

b. Short-fiber mass:

After the acid treatment, the collagen lumps are first ground twice in a meat grinder and then squeezed through a fine screen. There follows dilution to a concentration of 2.2 wt. % and homogenization by passing three times through a colloid mill. The fibers and the short-fiber mass are now mixed with one another in a ratio of 2:3 and the pH brought to 9 with diluted NaCl. 4 wt. % Triton-X-100 (based on dry weight) are added. Stirring time is about 5 minutes (non-ionic emulsifier, ethoxylated octylphenol, 9 to 10 ethoxy groups).

2% Hexamethylene diisocyanate are now added to the mass (calculated on dry weight), the mass introduced into molds and frozen overnight in a freezing cell at −25° C. The material is then freeze-dried and split to a thickness of 2 mm.

EXAMPLE 2

Cattle necks are prepared as in Example 1 and treated with NaOH and hydrogen peroxide. After washing in the hollander, the maturing process is carried out by means of enzymes as follows:

The material is weighed into a tanners vat. The ratio of liquid to hide is 2:1. The material is thoroughly stirred, the pH is adjusted with sodium hydroxide to 10.5, and there is then added to this material 1% of a mixture (based on gross weight) of the following components:

10% alkaline bacterial proteinases from Bacillus subtilis of 9000 LVU
40% urea
50% ammonium sulphate.

After a period of reaction lasting 5 days with periodic stirring (5 minutes every 2 hours), the enzymatic treatment is completed. There follows an acid treatment and processing as in Example 1. Both sponges are very soft velour-like and excellently suited for all medical or cosmetic uses.

It will be appreciated that the instant specification and examples are set forth by way of illustration and not limitation, and that various modifications and changes may be made without departing from the spirit and scope of the present invention.

We claim:

1. A process for producing collagen sponge which is insoluble but highly swellable in water, the sponge having a velour-like surface and being particularly suited for medical and cosmetic applications, comprising dehairing animal hides, enzymatically degrading the hides to form a collagen-containing mass, digesting the mass in acid or alkali to reduce the amido nitrogen content thereof to below about 0.25 mol %, swelling the mass in acid, comminuting part of the swollen mass to a fiber length of about 1 cm and a part to a fiber length of about 1 mm, forming a paste in water of about 0.5 to 3 weight % of a mixture which on a dry basis comprises about 20 to 60 weight % of the 1 cm fibers and about 80 to 40 weight % of the short fibers, adjusting the pH to about 2 to 3.5, cross-linking the paste in the presence of a cross-linking agent at a temperature below about 0° C. to form a swollen sponge of high purity, and removing water from the swollen sponge.

2. The process according to claim 1, wherein the cross-linking of the collagen sponge is effected at a temperature from about −5° to −60° C.

3. The process according to claim 1, wherein alkaline degradation of the collagen-containing raw material is effected at a pH above 10 with a solution of about 0.1 to 1% hydrogen peroxide in aqueous soda lye.

4. The process according to claim 1, wherein the enzymatic degradation is effected in the presence of about 0.1 to 1 mol/l of urea and alkaline proteinases at a pH between about 9 and 13, or with acid proteinases at a pH between about 2 and 5.

5. The process according to claim 4, wherein as proteinases there are employed proteinases from *Bacillus alkalophillis, Bacillus firmus, Bacillus licheniformis, Aspergillus Oryzae, Aspergillus Saitoi* or *Streptomyces griseus.*

6. The process according to claim 1, wherein the cross-linking agent is an aliphatic, aromatic or hydroaromatic diisocyanate.

7. The process according to claim 1, wherein cross-linking is effected in the presence of about 0.1 to 6%, based on the dry weight of the collagen material, of an emulsifier comprising a physiologically compatible ethoxylated alkylphenol or alcohol.

8. The process according to claim 1, wherein during cross-linking a cosmetic, diagnostic and/or pharmaceutically active substance is added in a concentration of about 1 to 50% based on the dry weight of the collagen material, thereby to be incorporated into the resulting sponge.

9. The process according to claim 1, wherein removal of water from the sponge is effected by first shock freezing at a pH between about 2.5 and 3.5 at a temperature between about −20° and −40° C., and then freeze drying.

10. A collagen sponge produced by the process of claim 1.

* * * * *

UNITED STATES PATENT AND TRADEMARK OFFICE
CERTIFICATE OF CORRECTION

PATENT NO. : 4,320,201
DATED : March 16, 1982
INVENTOR(S) : Alexander Berg et al It is certified that error appears in the above—identified patent and that said Letters Patent is hereby corrected as shown below:

On the title page insert

-- (30) Foreign Application Priority Data

October 27, 1979   Germany   2943520 --

Signed and Sealed this

Twenty-fifth Day of May 1982

[SEAL]

Attest:

Attesting Officer

GERALD J. MOSSINGHOFF

Commissioner of Patents and Trademarks